US00PP25939P2

(12) United States Plant Patent
Meerow

(10) Patent No.: US PP25,939 P2
(45) Date of Patent: Sep. 22, 2015

(54) ***HIPPEASTRUM* PLANT NAMED 'MIAMI'**

(50) Latin Name: ***Hippeastrum* Herb.**
Varietal Denomination: Miami

(71) Applicant: The United States of America, as represented by the Secretary of Agriculture, Washington, DC (US)

(72) Inventor: Alan W Meerow, Davie, FL (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 10 days.

(21) Appl. No.: 13/987,958

(22) Filed: Sep. 18, 2013

(51) Int. Cl.
*A01H 5/02* (2006.01)

(52) U.S. Cl.
USPC ..... Plt./402

(58) Field of Classification Search
USPC ..... Plt./402
See application file for complete search history.

*Primary Examiner* — Anne Grunberg
(74) *Attorney, Agent, or Firm* — Gail E. Poulos; John D. Fado; Lesley Shaw

(57) ABSTRACT

A new and distinct tetraploid 2n=44 *Hippeastrum* interspecific hybrid plant named 'Miami' measuring approximately 11-14 cm long, approximately 14-16 cm wide laterally, 16-17.5 cm wide dorsal-ventrally. The flowers are densely striated orange red approximately RHS Orange Red 33A on their inner surfaces, with a sharp white RHS 155C keel.

3 Drawing Sheets

Latin name of the genus and species of the plant claimed: 'Miami' is a new amaryllis plant that is a *Hippeastrum* Herb.

Variety denomination: The amaryllis plant claimed is of the variety denominated 'Miami', *Hippeastrum* Herb.

BACKGROUND OF THE INVENTION

The present invention is a new and distinct interspecific hybrid of *Hippeastrum* Herb., commonly known as amaryllis, a member of the family Amaryllidaceae, and is henceforth referred to by the cultivar name 'Miami'.

'Miami' originated as a cross made by the inventor in 2004 as part of a breeding program in Miami, Fla., USA. The objectives of the breeding program are to develop new amaryllis varieties with novel floral form and coloration and heat tolerance. The female parent is *Hippeastrum* 'Mount Blanc'× [(*H. ambiguum*×*H. papilio*)×*H.* 'Bouquet'] labeled with the breeder's code 609-04-1. The pollen parent is a proprietary selection of the cross [(*Hippeastrum ambiguum*×*H. papilio*)× *H. brasilianum*]×'Wonderland' named 'Orlando'.

The new cultivar was selected on the basis of its intense orange red color contrasted by a broad median white stripe on the tepals. Over the course of five years of evaluation, 'Miami' has shown excellent heat resistance, grown under ambient conditions in Miami, Fla. under 50% shade, and resistance to Red Scorch fungus (*Staganospora curtisii*).

Asexual reproduction of the new cultivar by twin-scale cuttings taken in a controlled environment in Miami, Fla. has shown that the unique features of this new amaryllis are stable and reproduced true to type in successive generations.

SUMMARY OF THE INVENTION

The following traits have been repeatedly observed and are determined to be the unique characteristics of 'Miami'. It is contrasted with its parents in Table 1. This characteristic distinguishes 'Miami' as a new and distinct cultivar:

1) Unique bright red-orange, RHS 33A and white RHS 155D, coloration pattern that has not been seen in currently available commercial cultivars.
2) Additionally, 'Miami' shows resistance to Red Scorch fungus (*Staganospora curtisii*) and high temperatures, approximately 30-35° C., as do its parents.

TABLE 1

Comparison of *Hippeastrum* 'Miami' and its two parent plants.

| Characteristic | 'Miami' | Clone 609-04-1 | 'Orlando' |
|---|---|---|---|
| No. scapes per season | 2-3 | 2-3 | 3 |
| Scape height (cm) | 45-55 | 40-55 | 40-60 |
| No. firs. per scape | 4 | 4 | 4 |
| Flr color | Red-orange and white | Orange | Cerise pink and white |

Of the numerous commercial cultivars of amaryllis familiar to the inventor, the most similar to the new *Hippeastrum* 'Miami' is *Hippeastrum* 'Orlando' (Plant patent application Ser. No. 13/987,957), from which 'Miami' differs by the intense red-orange approximately RHS Orange Red 33A color of the tepals.

BRIEF DESCRIPTION OF THE PHOTOGRAPHS

Figure 1A:
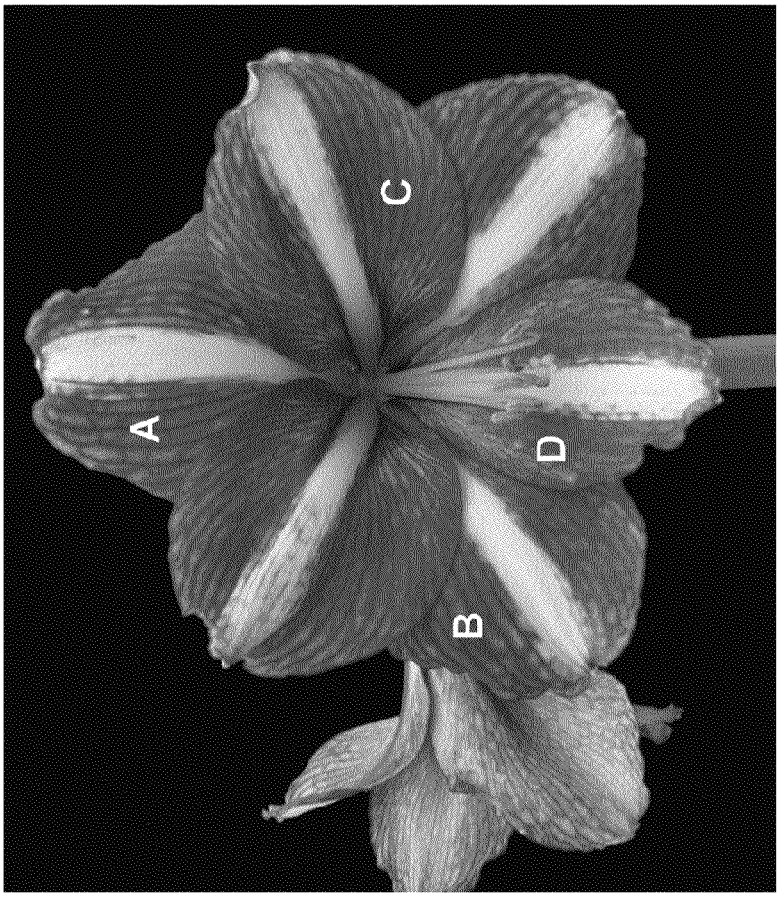
Figure 1B:
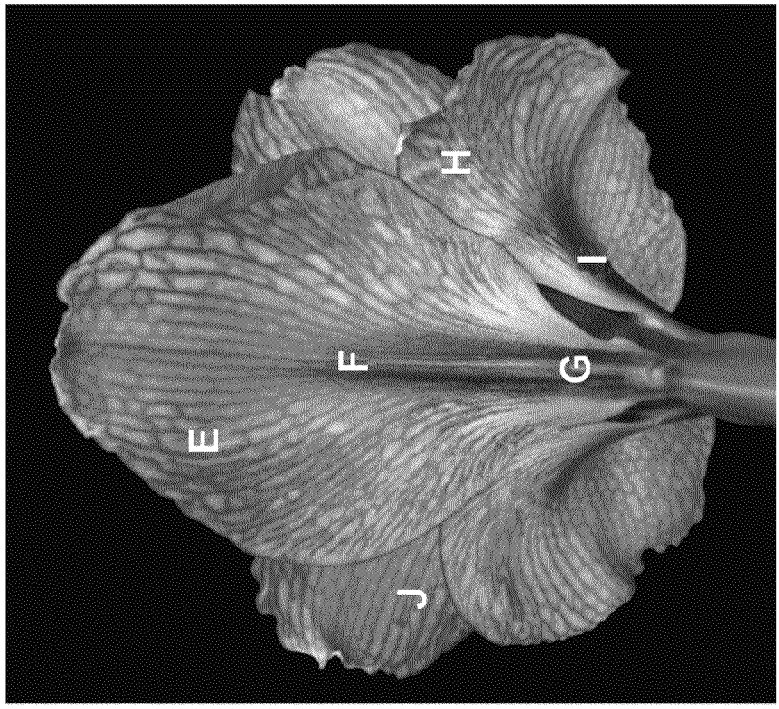

FIGS. 1A and 1B. Gray scale pictures of the flowers of *Hippeastrum* hybrid 'Miami' showing the locations of colorimeter readings in Table 2 below.

Figure 2:
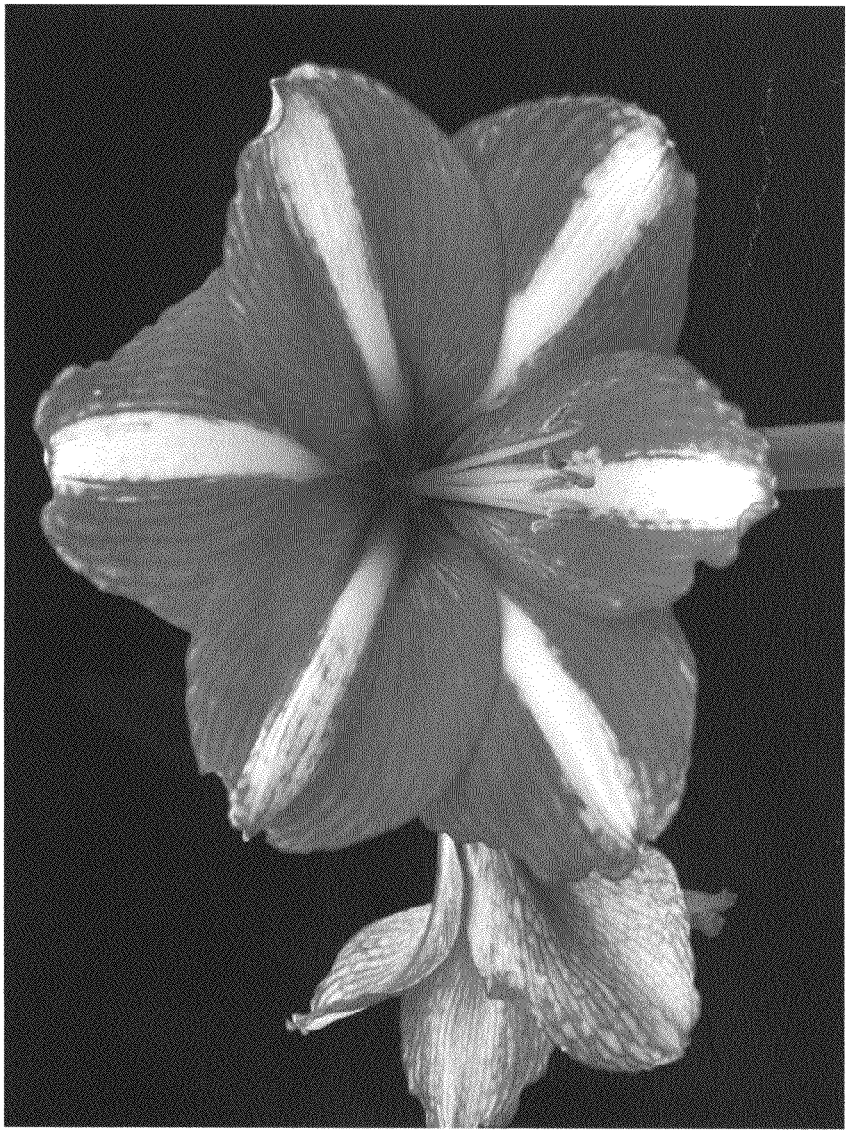
Figure 3:
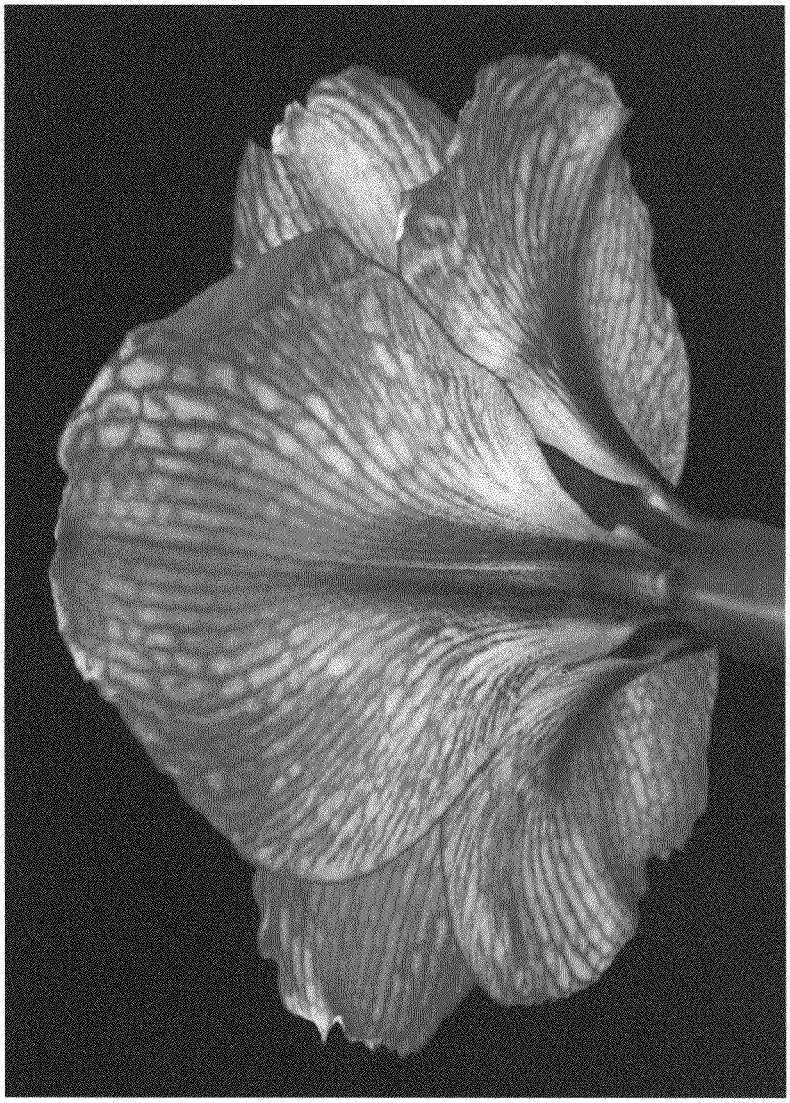

FIGS. 2 and 3 are photographs of the flower of *Hippeastrum* hybrid 'Miami'.

DETAILED BOTANICAL DESCRIPTION

The cultivar Miami has not been observed under all possible environmental conditions. The phenotype may vary somewhat with variations in environment such as temperature, daylength and light intensity, without, however, any variance in genotype.

Color descriptions below are based on evaluations with a Minolta CR-400 colorimeter at CIE D65/2$^0$ illumination/viewer conditions. The color parameters correspond to the uniform color space CIELAB, derived from Gonnet (Journal of Horticultural Science, Volume 68, 499-510, 1993; Food Chemistry, Volume 63, 409-415, 1998). Two color coordinates, a* and b*, as well as a psychometric index of lightness, L*, are defined. The L* is a measurement of luminosity, i.e., the equivalence of each color on the gray scale, ranging from 0 (black) to 100 (white). The a* takes positive values (0 to +60) for reddish colors and negative values (0 to −60) for the greenish ones, whereas the b* takes positive values (0 to +60) for yellowish colors and negative values (0 to −60) for the bluish ones. This is much more precise and repeatable analysis of color than obtained by using color charts (Ayala-Silva and Meerow, Proc. Intl. Trop. Hort. Soc., Volume 50, 138-144, 2006). The colorimeter takes three consecutive measurements of each sample, which was repeated three times, thus each set of color coordinates obtained are means of nine measurements. Where a reasonably close match could be discerned, The R.H.S. Colour Chart (Royal Horticultural Society, London, England, 1966) is also referenced.

TABLE 2

Colorimeter readings under the CIELAB color space for various locations on the flowers of *Hippeastrum* hybrid 'Miami'. See text for explanation of the values.

| Location (see FIG. 1) | | L*(C) | a*(C) | b*(C) |
|---|---|---|---|---|
| A | MEAN | 46.82 | 60.51 | 55.47 |
| | STDEV | 0.03 | 0.03 | 0.08 |
| B | MEAN | 49.09 | 55.28 | 47.16 |
| | STDEV | 1.84 | 1.71 | 1.26 |
| C | MEAN | 48.87 | 56.43 | 51.90 |
| | STDEV | 1.19 | 0.77 | 1.44 |
| D | MEAN | 56.00 | 50.98 | 47.28 |
| | STDEV | 0.90 | 0.37 | 0.24 |
| E | MEAN | 59.12 | 37.75 | 21.08 |
| | STDEV | 0.22 | 2.42 | 0.91 |
| F | MEAN | 62.51 | 38.24 | 23.43 |
| | STDEV | 0.04 | 0.11 | 0.16 |
| G | MEAN | 57.65 | 24.99 | 18.61 |
| | STDEV | 0.14 | 0.06 | 0.16 |
| H | MEAN | 66.20 | 27.82 | 17.65 |
| | STDEV | 0.33 | 0.84 | 0.42 |
| I | MEAN | 52.72 | 4.08 | 23.82 |
| | STDEV | 0.44 | 0.23 | 0.17 |
| J | MEAN | 67.22 | 29.10 | 15.16 |
| | STDEV | 0.32 | 0.94 | 0.39 |
| lateral inner tepal abaxial (lower keel) | MEAN | 53.16 | 24.91 | 18.84 |
| | STDEV | 0.94 | 0.87 | 0.76 |
| ventral inner tepal abaxial | MEAN | 74.28 | 21.85 | 13.19 |
| | STDEV | 0.06 | 0.07 | 0.05 |
| ventral inner tepal abaxial (lower keel) | MEAN | 68.92 | 33.07 | 18.95 |
| | STDEV | 0.06 | 0.07 | 0.05 |
| ventral inner tepal abaxial (mid keel) | MEAN | 78.87 | 19.68 | 12.22 |
| | STDEV | 0.13 | 0.08 | 0.04 |

Botanical classification: *Hippeastrum* hybrid cultivar Miami.

Parentage:

*Female or seed parent.*—Proprietary selection of *Hippeastrum* 'Mount Blanc'×[(*H. ambiguum*×*H. papilio*)×*H.* 'Bouquet'] labeled with the breeder's code 609-04-1, not patented.

*Male or pollen parent.*—Proprietary selection of the cross [(*Hippeastrum ambiguum*×*H. papilio*)×*H. brasilianum*]×'Wonderland' named 'Orlando'.

Propagation:

*Type.*—Twin-scale cuttings (division of the mother bulb into vertical segments and twin-scale units).

*Time to initiate roots, summer.*—About 30 days at temperatures of 30° C.

*Time to initiate roots, winter.*—About 40 days at temperatures of 22° C.

*Time to develop roots, summer.*—About 65 days at temperatures of 30° C.

*Time to develop roots, winter.*—About 90 days at temperatures of 22° C.

Plant description:

*Appearance.*—Perennial herbaceous amaryllis. Upright and clumping growth habit, moderately tall.

*Crop time.*—From bulb scale cuttings, about two years are required to produce a finished, flowering plant in a 15 to 20-cm container.

*Vigor.*—Moderately vigorous.

*Plant height.*—About 60 cm.

*Plant spread.*—About 70 cm.

Roots: White; numerous; fine and fibrous to moderately thick and fleshy; produced from basal plate of bulb; freely branching.

Bulb:

*Diameter.*—Approximately 6-11 cm.

*Circumference.*—Approximately 18-35 cm.

*Shape.*—Ovoid.

*Color.*—RHS 149A; tunic, RHS 165A.

*Offsets produced per year.*—Two to three offsets per bulb.

Foliage description:

*Arrangement.*—Distichous.

*Quantity.*—4-8 per bulb.

*Length, mature leaves.*—Approximately 50-65 cm early in season, approximately 76-82 cm late in season.

*Width, mature leaves.*—About 3.5-6.0 cm.

*Shape.*—Lorate.

*Apex.*—Acute.

*Margin.*—Entire.

*Texture.*—Coarse; glabrous.

*Color.*—Young foliage, upper surface: RHS 144A. Young foliage, lower surface: RHS 144B. Mature foliage, upper surface: L*(C)=39.84, a*(C)=−16.02, b*(C)=23.02. Mature foliage, lower surface: L*(C)=46.92, a*(C)=−16.82, b*(C)=26.76.

Flower description:

*Appearance.*—Wide spreading funnel-shaped single flowers arranged in umbels borne on a leafless scape. Corolla and calyx similar (tepals), three-parted and fused at the base. Freely flowering, typically four open flowers per scape and eight flowers and flower buds per plant. Flowers last about three or four days each. Flowers persistent. Flowers held perpendicular to the scape.

*Flowering response.*—Plants flower in the spring. Plants typically flower about March 15 to April 15 in Miami, Fla.

*Fragrance.*—Not detected.

*Scape.*—Length: approximately 45-55 cm. Diameter: About 1.5 cm. Appearance/aspect: Leafless; upright; not fasciated, hollow. Strength: Moderate. Texture: Smooth. Color: 137D.

*Pedicel.*—Approximately 4-5.5 cm long.

*Flower length.*—Approximately 11-14 cm.

*Flower diameter.*—Approximately 14-16 cm.

*Flower depth* (*height*).—Approximately 16-17.5 cm.

*Flower buds*.—Length: about 4 cm. Width: about 1 cm. Shape: Oblanceolate. Color: close to RHS 155D in lower half, RHS 33A in upper half. Rate of flower bud opening: about 2 days each, all flower opening in 8-10 days.

*Tepals*.—Number: six, in two whorls of 3. Fused and forming tube in proximal 2 cm. Outer whorl: Length: Approximately 12.0-12.5 cm. Width: Approximately 7.5-8.2 cm. Shape: broadly ovate. Apex: apiculate. Margin: coarsely undulate. Texture: Smooth; petals appear luminous and crystalline. Color: upper surface: densely striated RHS 33A, especially upper surface (Table 2), green RHS 144B at base, with median pure white keels RHS 155D approximately 1.3-1.5 cm wide; lower surface striations more diffuse, with white RHS 155D background, keel darker, and suffused with green RHS 144C on either side in the lower ½. Inner whorl — Length: Approximately 11.2-12 cm, ventral: Approximately 12-12.2 cm; width: Approximately 6.7-7 cm ventral: Approximately 5-5.5 cm. Shape: ovate, the ventral tepal narrower. Apex: apiculate. Margin: coarsely undulate. Color: both surfaces: as per outer whorl, but dark markings at throat more pronounced on laterals (Table 2).

*Throat*.—Green RHS 144B, with lacinate fimbrae.

*Reproductive organs*.—Androecium: Stamen number: Six. Length: Approximately 7.8-9.4 cm; filaments speckled red-orange RHS 33A in their distal ½, fading to white RHS 155D and finally green RHS 151B in their proximal ⅓-¼. Anther shape: Elliptic. Anther size: About 7 mm. Anther color: white RHS 155D. Pollen amount: Moderate. Pollen color: yellow RHS 3C. Gynoecium: Pistil number: One. Pistil, length: About 10.5-11.7 cm. Stigma shape: tri-lobed. Stigma width: about 6 mm. Stigma color: white RHS 155D, red-orange RHS 33A at margins. Style color: diffusely specked red-orange RHS 33S, fading to white RHS 155D then green RHS 151B in proximal 2 cm. Ovary shape: ellipsoid, ovary length: Approximately 20-23 mm, ovary width: Approximately 8-10 mm, ovary color: RHS 141C.

*Seed*.—Seed development has not been observed.

Chromosome number: 2n=44. Plant is tetrapolid.

Disease resistance: Plants of the new amaryllis appear resistant to Red Scorch Fungus (*Staganospora curtisii*).

Heat tolerance: Plants of the new amaryllis have demonstrated good tolerance to high temperatures about 30 to 35° C.

I claim:

1. A new and distinct cultivar of amaryllis genus *Hippeastrum* named 'Miami', as illustrated and described.

* * * * *